(12) United States Patent
Henning et al.

(10) Patent No.: US 9,791,386 B2
(45) Date of Patent: Oct. 17, 2017

(54) INTEGRATED, PORTABLE SAMPLE ANALYSIS SYSTEM AND METHOD

(75) Inventors: Patrick F. Henning, Concord, MA (US); Thomas G. Barraclough, Maynard, MA (US); Eric J. Olson, Phillipston, MA (US); Stephen D. Lawrence, Ayer, MA (US); Robert J. Yurko, Chelmsford, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 838 days.

(21) Appl. No.: 13/374,934

(22) Filed: Jan. 24, 2012

(65) Prior Publication Data

US 2013/0191046 A1   Jul. 25, 2013
US 2017/0097308 A9   Apr. 6, 2017

Related U.S. Application Data

(63) Continuation-in-part of application No. 12/321,399, filed on Jan. 20, 2009, now Pat. No. 8,384,895.

(51) Int. Cl.
*G01F 1/74* (2006.01)
*G01N 23/06* (2006.01)
*G01N 21/3577* (2014.01)

(52) U.S. Cl.
CPC ......... *G01N 23/06* (2013.01); *G01N 21/3577* (2013.01)

(58) Field of Classification Search
CPC ............ G01F 1/74; G01F 9/001; G01F 9/006; G01F 25/0061; G01F 23/266; G01F 25/0084; G01N 9/00; G01N 11/06

(Continued)

(56) References Cited

U.S. PATENT DOCUMENTS

| 4,554,821 A | * | 11/1985 | Kiesewetter | ............. G01N 9/26 |
| | | | | 73/54.07 |
| 6,459,767 B1 | * | 10/2002 | Boyer | .................. G01N 23/223 |
| | | | | 378/121 |

(Continued)

FOREIGN PATENT DOCUMENTS

| CN | 101023348 A | 8/2007 |
| CN | 101137901 A | 3/2008 |

OTHER PUBLICATIONS

Written Opinion of the International Searching Authority, from International Application No. PCT/US2013/021407, dated Mar. 19, 2013, 7 pages. (unnumbered).

(Continued)

*Primary Examiner* — Gregory J Toatley
*Assistant Examiner* — Douglas Kay
(74) *Attorney, Agent, or Firm* — Iandiorio Teska & Coleman, LLP

(57) ABSTRACT

An integrated, portable sample analysis system and method. A viscometer subsystem receives a first portion of a sample. A spectrometer subsystem receives a second portion of the sample. A syringe pump subsystem receives a third portion of the sample and is configured to urge the third portion of the sample through a filter which collects particles in the sample thereon. An x-ray analysis subsystem is configured to x-ray the particles. The x-ray analysis subsystem also receives a fourth portion of the sample in order to determine the composition of any dissolved material in the sample. A processing subsystem provides a report concerning the sample and its viscosity, physical properties, particulate count and size distribution, and the composition of particulate and dissolved elements in the sample.

25 Claims, 18 Drawing Sheets

(58) Field of Classification Search
USPC ... 73/54.13, 54.07, 54.5, 114.52, 1.73, 54.04
See application file for complete search history.

(56) References Cited

U.S. PATENT DOCUMENTS

| | | | |
|---|---|---|---|
| 6,535,836 B1* | 3/2003 | Grace | G01N 15/12 |
| | | | 702/179 |
| 6,561,010 B2 | 5/2003 | Wilson et al. | |
| 6,582,661 B1 | 6/2003 | Pardue et al. | |
| 6,598,464 B1 | 7/2003 | Rossi | |
| 2001/0013247 A1* | 8/2001 | Wilson | G01N 33/2858 |
| | | | 73/54.01 |
| 2005/0041774 A1* | 2/2005 | Saitoh | B01D 46/0002 |
| | | | 378/53 |
| 2006/0207316 A1 | 9/2006 | Tyrell | |
| 2007/0121113 A1* | 5/2007 | Cohen | G01N 30/74 |
| | | | 356/432 |
| 2008/0134765 A1* | 6/2008 | Baek | G01N 11/08 |
| | | | 73/54.09 |
| 2009/0216464 A1 | 8/2009 | Kong et al. | |
| 2009/0216465 A1 | 8/2009 | Millet | |
| 2010/0182599 A1* | 7/2010 | Albin | G01J 3/02 |
| | | | 356/326 |
| 2011/0201099 A1* | 8/2011 | Anderson | G01N 21/05 |
| | | | 435/287.2 |

OTHER PUBLICATIONS

Anonymous, "Motor Oil Viscosity Grades Explained in Layman's Terms", AMSOIL, Oct. 20, 2007. [retrieved on Mar. 4, 2013]. Retrieved from the Internet: <URL: http://web.archive.org/web/20071020042355/http://www.upmpq.com/tech_articles/motoroil_viscosity/>entiredocument. (3 pages).

Complete In-Service Oil Analysis Laboratory, "Spectro Industrial Tribology Laboratory (ITL) Turnkey Solution", Spectro Inc., www.SpectroInc.com v2.5/Jun. 22, 2010, 4 pgs. (unnumbered).

* cited by examiner

FIG. 19A

| TotalOil | | | | | |
|---|---|---|---|---|---|
| File Zoom Tools Help | | | | | |
| Shell Rotella T (MIL-L-2104) | | LITTLETON DIRT | No ID | No ID | |
| SampID: LITTLETON DIRT | | 14 Dec 2010 | 14 Dec 2010 | 14 Dec 2010 | |
| Memory: 3648 KB  Trends ▲ | | 15:40 | 15:33 | 14:50 | |
| IR Properties | | | | | |
| AW Additive | % | 0 | 70.66 | 67.37 | 72.81 |
| Glycol | % | 3 | 0.00 | 0.00 | 0.00 |
| Nitration | abs/mm2 | 30 | 6.91 | 7.10 | 7.08 |
| Oxidation | abs/mm2 | 30 | 2.91 | 2.87 | 2.78 |
| Soot | %wt | 3 | 0.23 | 0.23 | 0.23 |
| Sulfation | abs?mm2 | 40 | 12.35 | 12.41 | 12.32 |
| TBN | mgKOH/g | 0 | 6.85 | 7.00 | 7.43 |
| Water | ppm | 3000 | 4.91 | 4.91 | 4.91 |
| Viscometer Properties | | | | | |
| Visc-40 | Cst | 1000 | 239.90 | 201.83 | 189.65 |

| By Asset | Non Asset | All | | Print | Main Menu | Back | ved signals
INTEGRATED, PORTABLE SAMPLE ANALYSIS SYSTEM AND METHOD

RELATED APPLICATIONS

This application is a continuation-in-part of U.S. patent application Ser. No. 12/321,399 filed Jan. 20, 2009, now U.S. Pat. No. 8,384,895, and claims the benefit of and priority thereto under 35 U.S.C. §§119, 120, 363, 365 and 37 C.F.R. §1.55 and §1.78, which is incorporated herein by reference.

FIELD OF THE INVENTION

The subject invention relates to tribology and fluid (such as fuel) monitoring.

BACKGROUND OF THE INVENTION

Fluids such as oil in machinery, vehicles, ship engines, and the like are often analyzed in an attempt to ascertain information about the condition of the oil and/or the equipment which uses the oil. A tribology laboratory may include an infrared spectrometer for analyzing contaminants (water, for example) present in the oil and the like, a viscometer for measuring the viscosity of the oil, and/or devices which analyze and/or classify particles in the oil. See the brochure "Spectro Industrial Tribology Laboratory (ITL)", www.spectroinc.com, incorporated herein by this reference.

Each instrument typically provides some information about the oil sample and a skilled technician and/or scientist then uses all the information to make a full analysis of the oil sample and to perhaps make a recommendation based on the analysis.

Laboratories, however, take time to report the results of the analysis. Lab equipment is also fairly expensive and complex. Also, less skilled employees cannot typically operate the laboratory equipment, fully understand or appreciate the information provided by the equipment, or make proper recommendations.

Portable tribology devices are also known such as the "FluidScan" IR spectrometer product available from Spectro, Inc. See also US Patent Application Publication No. 2010/0182599 incorporated herein by this reference. Some portable devices are fairly easy to use.

To date, however, known portable devices have not replicated the analysis capability of a tribology laboratory.

BRIEF SUMMARY OF THE INVENTION

In one aspect, the invention results in a portable, battery-operated and highly integrated sample analysis system configured to analyze a sample using several instruments, to process the analysis information, and to provide relevant data to the user on site. The system can be operated by a less skilled worker.

The subject invention results, at least in part, from the realization, in one particular example, that if a viscometer, IR spectrometer, particle counter and x-ray subsystem are integrated in a carryable case in such a way that portions of a sample can be easily presented to the different instruments, then the processing subsystem (also in the case) can be programmed to provide, on site, a report concerning the sample and its viscosity, physical properties, particulates, and the composition of dissolved and particulate material in the sample and to call attention to certain information concerning the sample.

The invention features, in one example, an integrated portable analysis system comprising a viscometer subsystem with a port for receiving a first portion of a sample and configured to output a signal corresponding to the viscosity of the sample. A spectrometer subsystem has a port for receiving a second portion of the sample and is configured to output signals corresponding to the physical properties of the sample. A syringe pump subsystem includes a port for receiving a third portion of the sample and is configured to urge the third portion of the sample through a filter which collects, counts and sizes particles in the sample thereon.

An x-ray analysis subsystem is configured to x-ray the particles and to output signals corresponding to the composition of the particles. The x-ray analysis subsystem also includes a port for receiving a fourth portion of the sample and is further configured to output signals corresponding to the composition of any dissolved material (e.g., metals) in the sample.

A processing subsystem is responsive to the viscometer subsystem, the spectrometer subsystem, and the x-ray analysis subsystem and is configured to process the signals corresponding to the viscosity of the sample, the physical properties of the sample, the composition of the particles, the number and size distribution of particles, and the composition of any dissolved material in the sample. A report is provided concerning the sample and its viscosity, physical properties, the particulates, and the composition of any dissolved material in the sample.

The system typically also includes a particulate cartridge with a filter for loading first in the syringe pump to collect particles on the filter and then in the x-ray analysis subsystem port for analysis of the composition of the particles. The preferred particulate cartridge includes a well filled with a wick and covered with the filter and an outlet port. The syringe pump subsystem may then include a bladder for receiving the third port portion of the sample which flows out of the outlet port of the well. The particulate cartridge usually includes a cover. The system may also include a liquid sample cartridge including a well for the fourth portion of the sample and configured to be inserted into the x-ray analysis subsystem port. The liquid sample cartridge also includes a cover.

The viscometer subsystem may include a flip-top sample cell including a first plate including a rail configured to constrain fluid thereon between its edges by surface tension and a second plate including a surface spaced from the rail by a predefined gap for constraining fluid to the rail by surface tension when the rail is inclined by gravity and pulls the fluid along the rail. The spectrometer subsystem may also include a flip-top sample cell including first and second hinged plates each including a window aligned with each other when the plates are coupled together defining a predefined spacing between the windows when the plates are coupled together as a port for the second portion of the sample.

A particle counter can be associated with the syringe pump subsystem and configured to provide signals concerning the number and size distribution of any particles in the third portion of the sample to the processing subsystem.

The system preferably includes a panel in a portable case housing the viscometer subsystem and the spectrometer subsystem. Another panel in the portable case houses the x-ray analysis subsystem and the syringe pump subsystem. The portable case further includes the processing subsystem and a battery pack for the viscometer subsystem, the spectrometer subsystem, the syringe pump subsystem, the x-ray analysis subsystem, and the processing subsystem. The case also includes a monitor. The processing subsystem is configured to display the report on the monitor. The processing subsystem may be configured to highlight data in the report above a predetermined threshold and/or below a predetermined threshold. The processing subsystem may further be configured to analyze any highlighted data and to provide a grade for the sample based on said highlighted data.

The invention also features a sample analysis method comprising taking a sample from an apparatus at a site, placing a first-portion of a sample in a viscometer, and analyzing the first portion of the sample in the viscometer and providing a signal corresponding to the viscosity of the sample. A second portion of the sample is placed in a spectrometer and the method includes analyzing the second portion of the sample in the spectrometer and providing one or more signals corresponding to physical properties of the sample. Particles are filtered out of a third portion of the sample and analyzed in an x-ray analysis subsystem which provides one or more signals corresponding to the composition of the particles. The method also includes placing a fourth portion of the sample in the x-ray analysis subsystem and analyzing the fourth portion of the sample in the x-ray analysis subsystem and providing one or more signals corresponding to dissolved material in the sample. The signals corresponding to the viscosity of the sample, the physical properties of the sample, the composition of the particles, and the dissolved materials in the sample are processed and a report at the site is generated concerning the sample and its viscosity, physical properties, particulates, and dissolved materials.

Filtering particles out of the third portion of the sample may include placing the third portion of the sample in a syringe pump and driving the third portion of the sample through a filter which collects the particles thereon. The method may further include counting and sizing the particles. Typically, the method further includes highlighting data in the report above a predetermined threshold and/or below a predetermined threshold and grading the sample based on the highlighted data. Performing the entire analysis protocol, cleaning of the entire system, and preparing it for the next sample analysis is achieved without the use of chemicals, solvents, or diluents. Any cleaning or analysis preparation can be achieved via the use of a shop rag or disposable wipe.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 19A-19B are views of report examples provided by the processing subsystem of FIG. 17 on the display shown in FIG. 17.

DETAILED DESCRIPTION OF THE INVENTION

Figure 1:
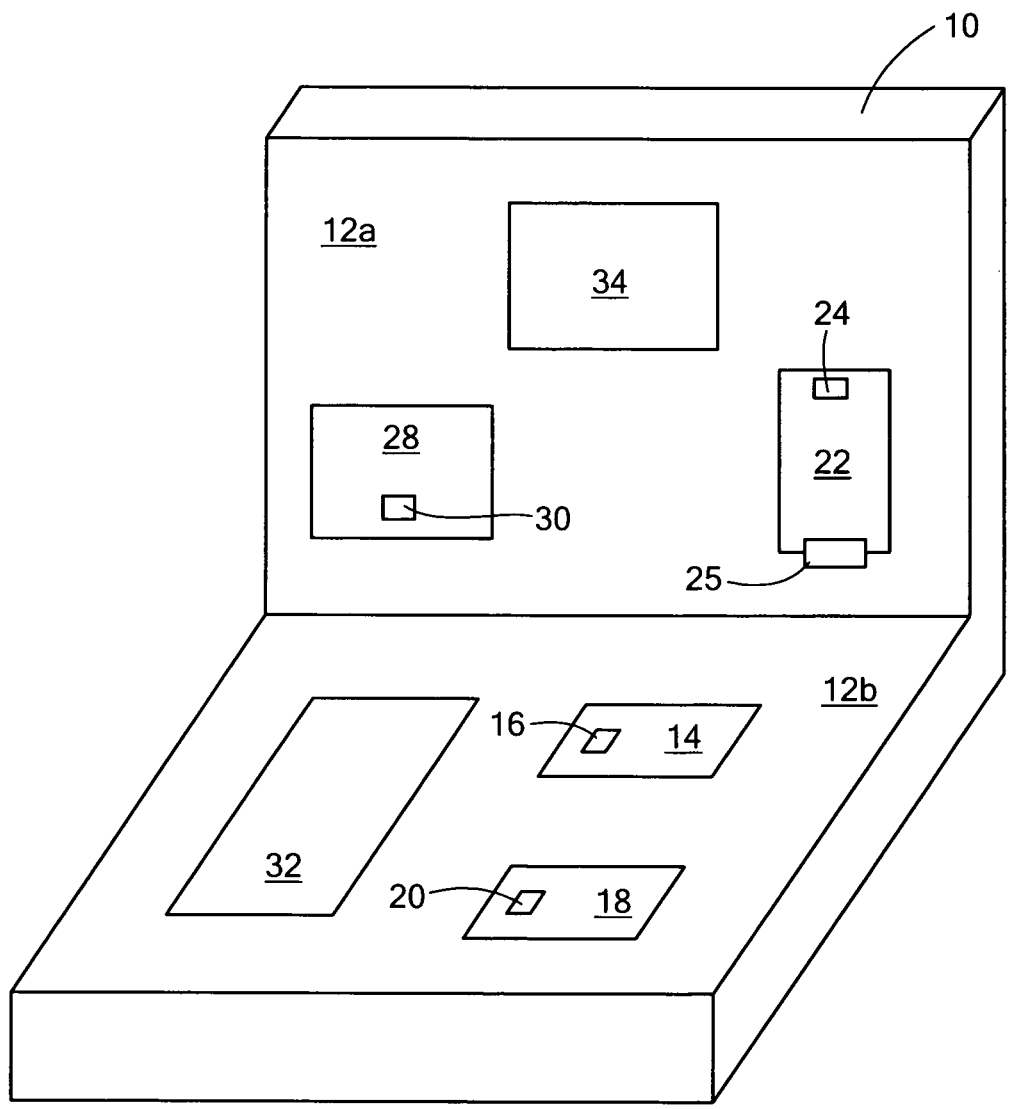
FIG. 1 is a block diagram showing several of the primary components associated with an integrated, portable sample analysis system in accordance with an example of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 schematically depicts portable analysis system according to one example of the invention integrated in portable brief case 10 including top interior panel 12a and bottom interior panel 12b. Viscometer 14 includes port 16 for receiving a first portion of a sample (e.g. an oil sample), using a syringe, for example. Viscometer 14 is configured to output a signal corresponding to the viscosity of the sample. Infrared spectrometer 18 includes port 20 for receiving a second portion of the sample and is configured to output signals corresponding to physical properties of the sample such as the amount of a contaminant like water present in the sample, acidity, and the like. In one example, the IR analysis properties are the % fuel contamination; % AW additive; % glycol; % by weight soot; ppm water; nitration (abs/mm$^2$), oxidation (abs/mm$^2$), sulfation (abs/mm$^2$) and TBN (mg-KOH/g) or TAN (mgKOH/g).

Syringe pump subsystem 22 includes port 24 for receiving a third portion of the sample. Syringe pump subsystem 22 is configured to urge the third portion of the sample through a filter (described below) which collects particles in the sample thereon. In one example, this filter is a component of a specially designed particulate cartridge received in outlet port 25. This particulate cartridge serves two key initial purposes: One, it is designed to behave as a pore blockage particle counting system in and of itself, which enables the user to obtain particle count (which includes number and size distribution), information from the device. Two, by monitoring the particle counting while the syringe is dispensing the oil liquid through the cartridge, it serves as a feedback loop to ensure that a consistent particulate deposition (e.g. total number of particles) occurs on the patch itself. This second purpose allows for a highly calibrated sample which significantly increases the accuracy of subsequent x-ray analysis. The particulate cartridge may be inserted into port 30 associated with x-ray analysis subsystem 28 which is configured to x-ray the particles on the filter and to output signals corresponding to the composition of the particles. In one example, the amount of elements (e.g., metals) such as Ag, Al, Cr, Cu, Fe, Mo, Ni, and Pb in ppm is determined.

A fourth liquid portion of the sample (unfiltered) may be deposited on a liquid sample cartridge which is also inserted into x-ray analysis subsystem 28 port 30 and the x-ray analysis subsystem then outputs signals corresponding to the composition and amount of any dissolved material (e.g., metals) in the sample. The total amount of particular metals (dissolved and undissolved) may be calculated and displayed.

A processing subsystem is also included as shown at 32 (e.g., a microprocessor, controller, or the like) and is responsive to the signals output by the viscometer, the infrared spectrometer, and the x-ray analyzer. Processing subsystem 32 is configured to process the signals corresponding to the viscosity of the sample, the physical properties of the sample, the composition of any particles present in the sample, and the composition of any particulate or dissolved material in the sample. The processing subsystem provides a report (for example, on monitor 34) concerning the sample and its viscosity, physical properties, particulates, and dissolved material and the like. Software operating on processing subsystem 32 is also configured to highlight certain select information about the sample based on its viscosity, physical properties, particulates, and/or dissolved material, etc. In but one example, if a value such as viscosity, ppm Ni, and/or % Glycol exceeds a maximum threshold or is below a minimum threshold, then the value may be displayed in red or otherwise highlighted. Trends can be reported, for example, by depicting on the screen, for a particular asset like an engine, the viscosity level for several samples taken at different times to indicate trend information. Trend information like a large jump from one example to another regarding the amount of iron present can be highlighted automatically for the user. The processing subsystem can even be programmed to make recommendations based on the outputs of the various analyzers and/or data sets over time.

Figure 2:
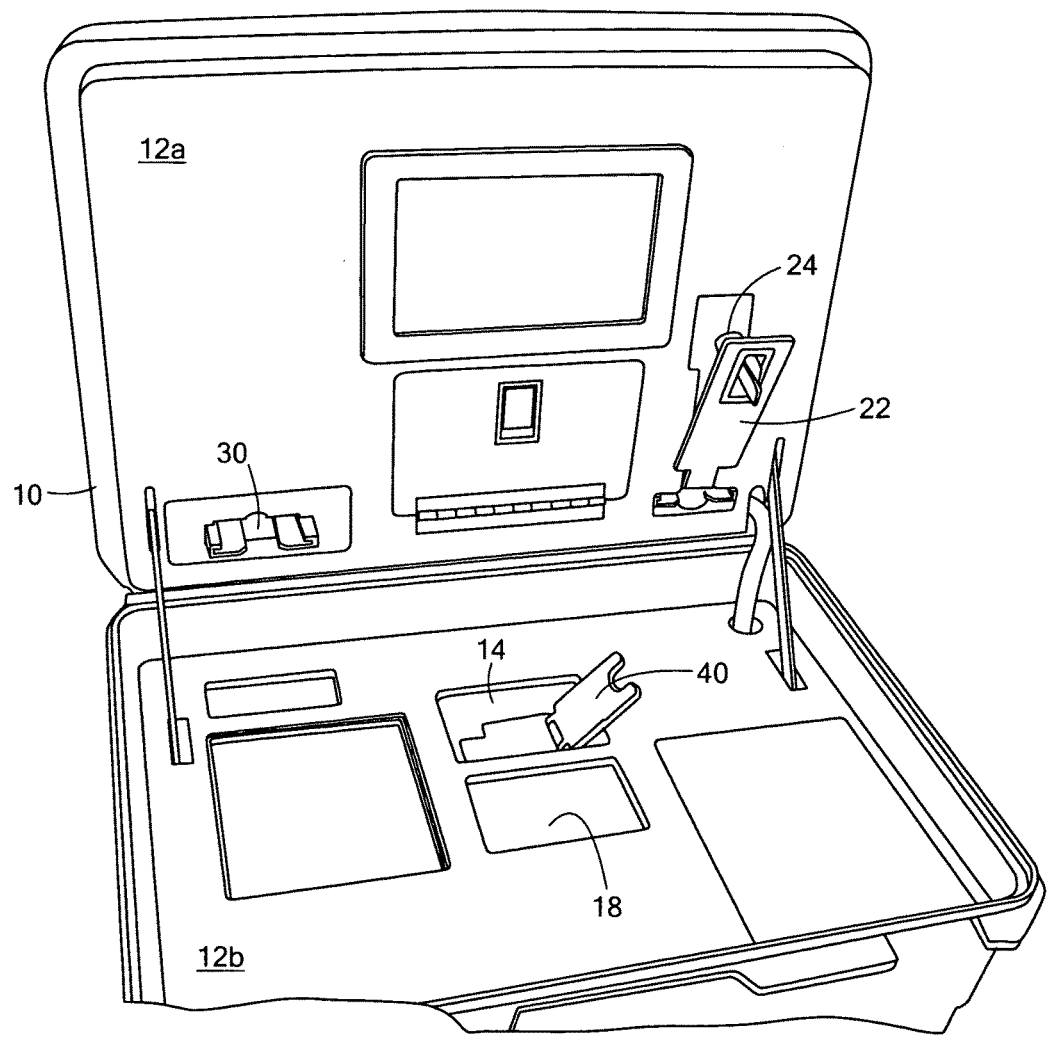
FIG. 2 is a three-dimensional front view showing a prototype of an integrated portable sample analysis system in accordance with the invention.
Figure 3:
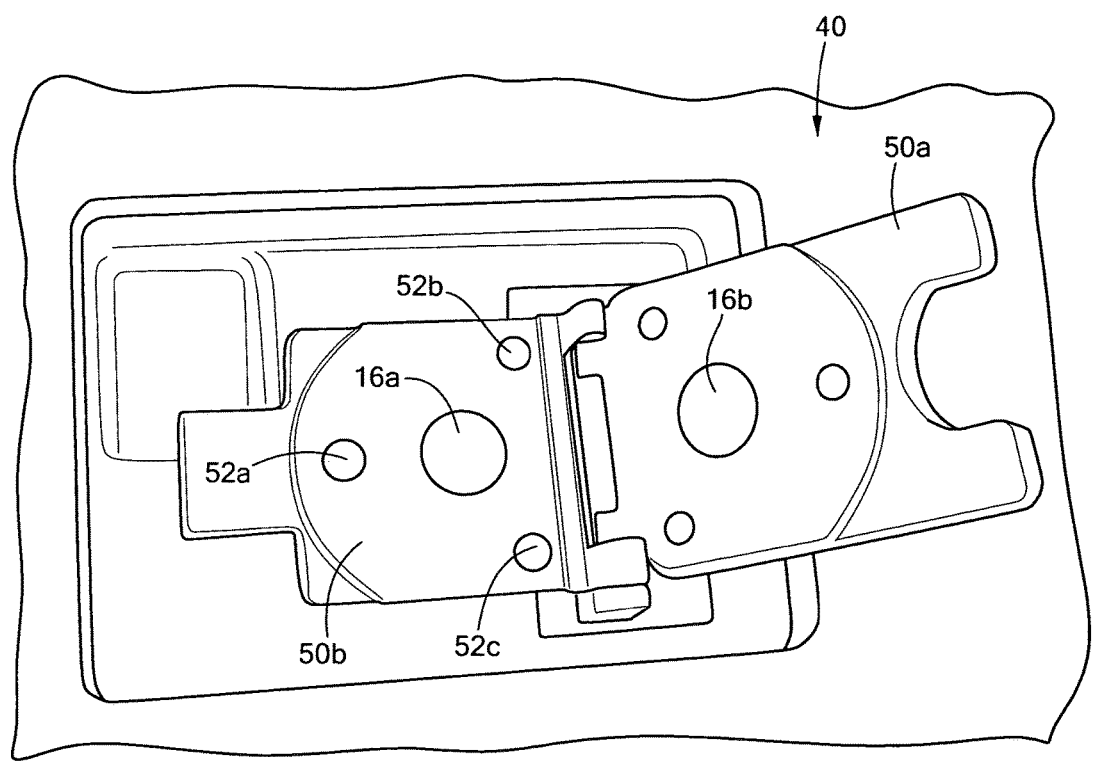
FIG. 3 is a three-dimensional view of a component of the spectrometer in the system shown in FIG. 2.

FIG. 2 shows one prototype unit. The x-ray analysis subsystem components are located behind interior panel 12a. The processing subsystem components are also located behind panel 12a but may also be present or distributed between panels 12a and 12b. One or more batteries may be located behind panel 12b. In FIG. 2, syringe pump/particle counter 22 is shown as is port 24 (see also FIG. 7) which receives a sample portion typically from a syringe. Infrared spectrometer flip-top cell 40 is shown in FIGS. 2 and 3. A portion of the sample is deposited on window port 16a, FIG. 3. This particular spectrometer component is further defined in US Patent Application Publication No. 2010/0182599 incorporated herein by this reference.

The analyzer of the IR spectrometer subsystem (located behind panel 12b, FIG. 2) typically provides information concerning the physical properties of the sample (e.g., % water, oxidation) to the processing subsystem which can be programmed to highlight data based on the physical properties and, in one preferred embodiment, the information provided by the viscometer, particle counting and x-ray subsystems.

In this example, the spectrometer subsystem includes flip-top cell 40 with hinged plates 50a and 50b, each including a window 16a and 16b. When the plates are coupled together, there is a predefined spacing between windows 16a and 16b for the second portion of the sample deposited via a syringe. Kinematic mounts 52a, 52b, and 52c define the spacing. Magnets can be used to releasably couple the plates together.

Viscometer subsystem 18 is also shown in FIG. 2 and FIGS. 4-6. In one particular example as described in FIG. 4, a kinematic viscometer includes flip-top cell 19 with first plate 110a with at least one rail 112 thereon raised from plate floor 114 and extending from proximal (e.g., top) end 116a to distal (e.g., bottom) end 116b. Rail 112 in one prototype example was 918 µm in width, between 0.01 and 0.02 inches high, and between 2 and 3 inches long. The top surface of rail 112 was flat to 16 RMS and +/1 degree. Rail 112 is thus configured to constrain a fluid thereon between edges 118a and 118b of the rail by surface tension.

Second plate 110b is typically hinged to plate 110a as shown at 120 and includes flat surface 122 to 116 RMS and +/1 degree over rail 112 separated there from by a predetermined gap (e.g., 100-200 µm) and thus constrains fluid to the rail by surface tension when rail 112 (and plate 10a) is inclined (e.g., positioned vertically) and gravity pulls fluid along the rail from proximal end 116a to distal end 116b. Typically, the gap is much less than 9 times the width of the rail.

In this particular design, plate 110b includes spaced recessed positive face magnets 130a, 130b, and 130c and plate 110a includes corresponding negative face magnets 132a, 132b, and 132c received in raised flat lands 144c, 146b, and 146d, respectively. Lands 144c, 146b, and 146d may be the same height as rail 112. Magnets 130 and 132 releasably couple plate 110a to plate 110b in order for plates 110a and 110b to be used for viscosity measurements and then separated (via the hinge) for cleaning. Alternatively, items 130a-130c could be magnets and items 132a-132c could be ferromagnetic material. The relative position of the magnets and/or the ferromagnetic material in the respective plates could also be reversed.

To properly space surface 122 of plate 110b over rail 112 by a specific (e.g., 100 µm) gap when the two plates are coupled together, kinematic mounts 136a-136c are disposed in plate 110b as shown and mate with disks 138a-138c, respectively. Disk 138a-138c are disposed flush in lands 144d, 144b, and 146c, respectively, which also typically have a height the same as the height of rail 112. The same is true for lands 144a and 146a. Other means for providing a predefined gap between the top surface of rail 112 and plate 110b, however, are within the scope of the subject invention. See also U.S. Patent Application Publication No. 2010/0182599 incorporated herein by this reference.

As shown, lands 144a-144d are spaced from each other and they are also spaced from rail 112 on one side of rail 112 while lands 146a-146d are spaced from rail 112 on the opposite side of rail 112. This arrangement, in turn, defines cross wise channels 150a and 150b, 152a and 152b, and 154a and 154b. Electromagnetic energy (e.g., laser light or LED light) can be directed in these channels in order to measure the velocity of a fluid sample moving along rail 112 as discussed below.

In this particular embodiment, rail 112 also has proximal end 160 defining a well with ramp 162 sloping upwards to the rail top surface. Rail 112 divides into split fingers 164a and 164b on opposite sides of ramp 162. Ramp 166 may also be provided in plate 110b as shown to further define the fluid sample well. Various materials may be used for plates 110a and 110b including aluminum and stainless steel and typically all the features shown are machined or otherwise formed on the surfaces of the respective plates.

Figure 4:
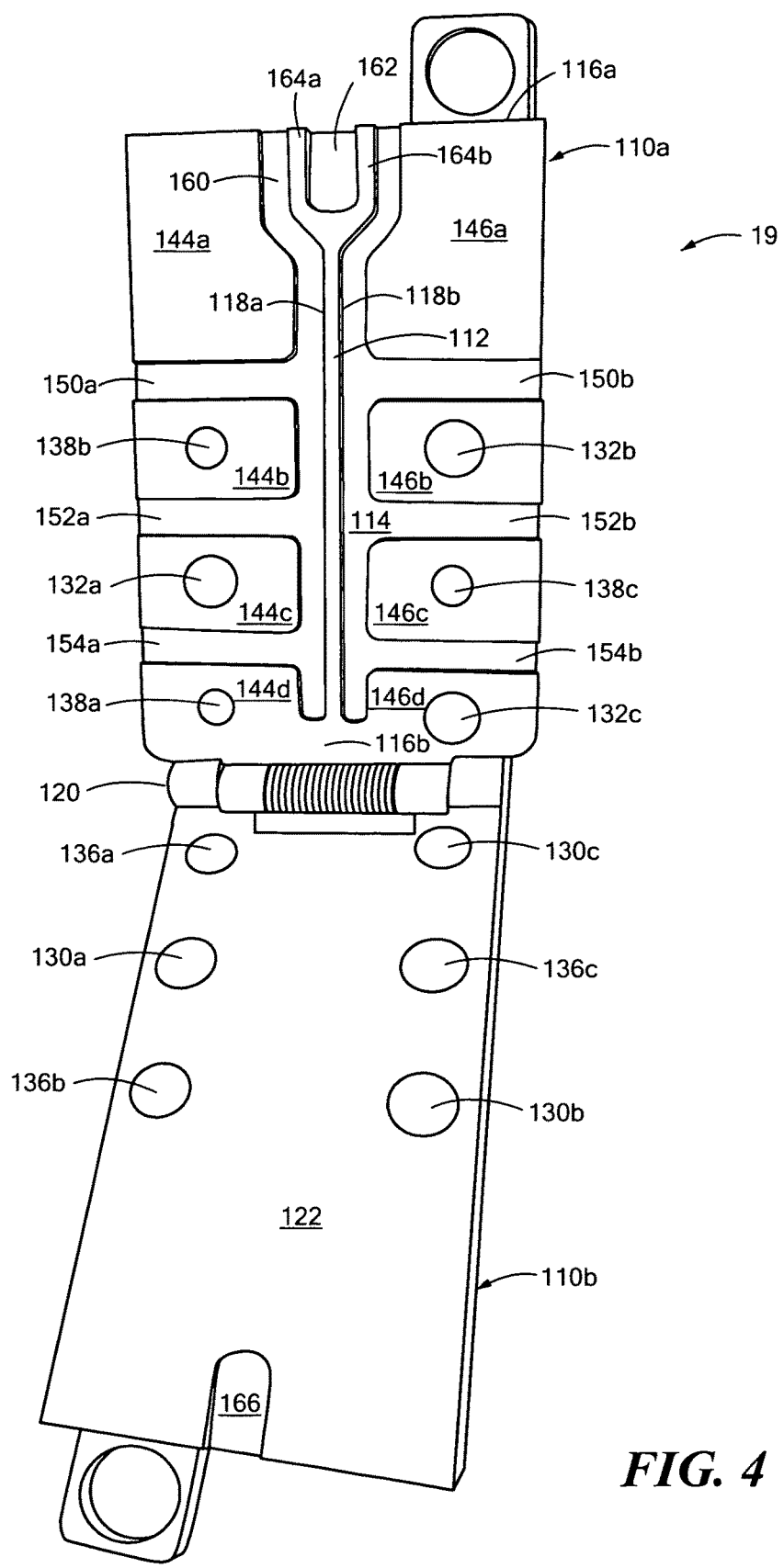
FIG. 4 is a schematic three-dimensional front view showing a component of the viscometer in the system shown in FIG. 2.
Figure 5:
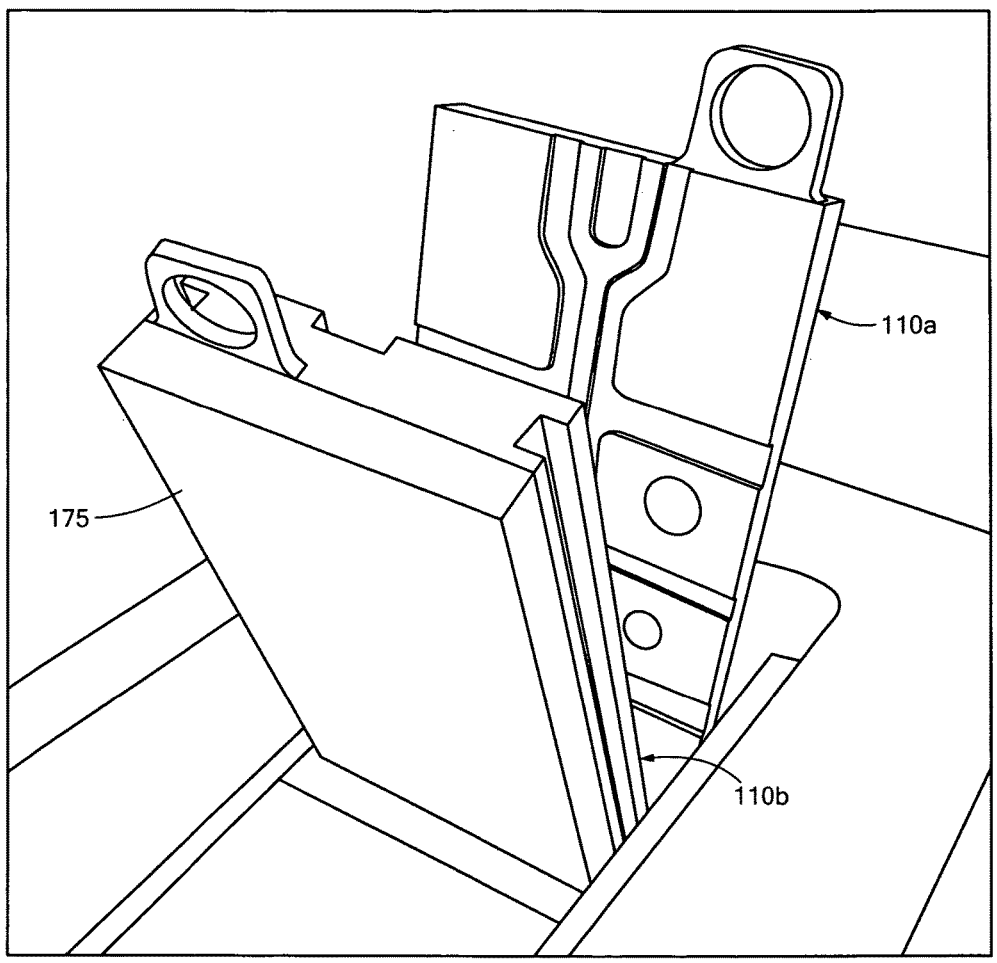
FIG. 5 is a schematic three-dimensional front view showing the viscometer component of FIG. 4 being inserted down into the viscometer analysis subsystem.

FIG. 5 shows plates 110a and 110b being folded up into a coupled relationship where rail 112, FIG. 4 is now oriented vertically and plate 110b is releasably coupled to plate 110a via magnets 130a-130c and 132a-132c and surface 122 of plate 110b is spaced by a predefined gap over the top surface of rail 112 by kinematic mounts 136a-136b. Once plates 110a and 110b are vertically disposed, they are urged downward into an analysis unit behind panel 12b, FIG. 2. FIG. 5 also shows heater element 175 on the rearward surface of plate 110b for heating the sample to a predefined temperature, for example 40° C.

Figure 6:
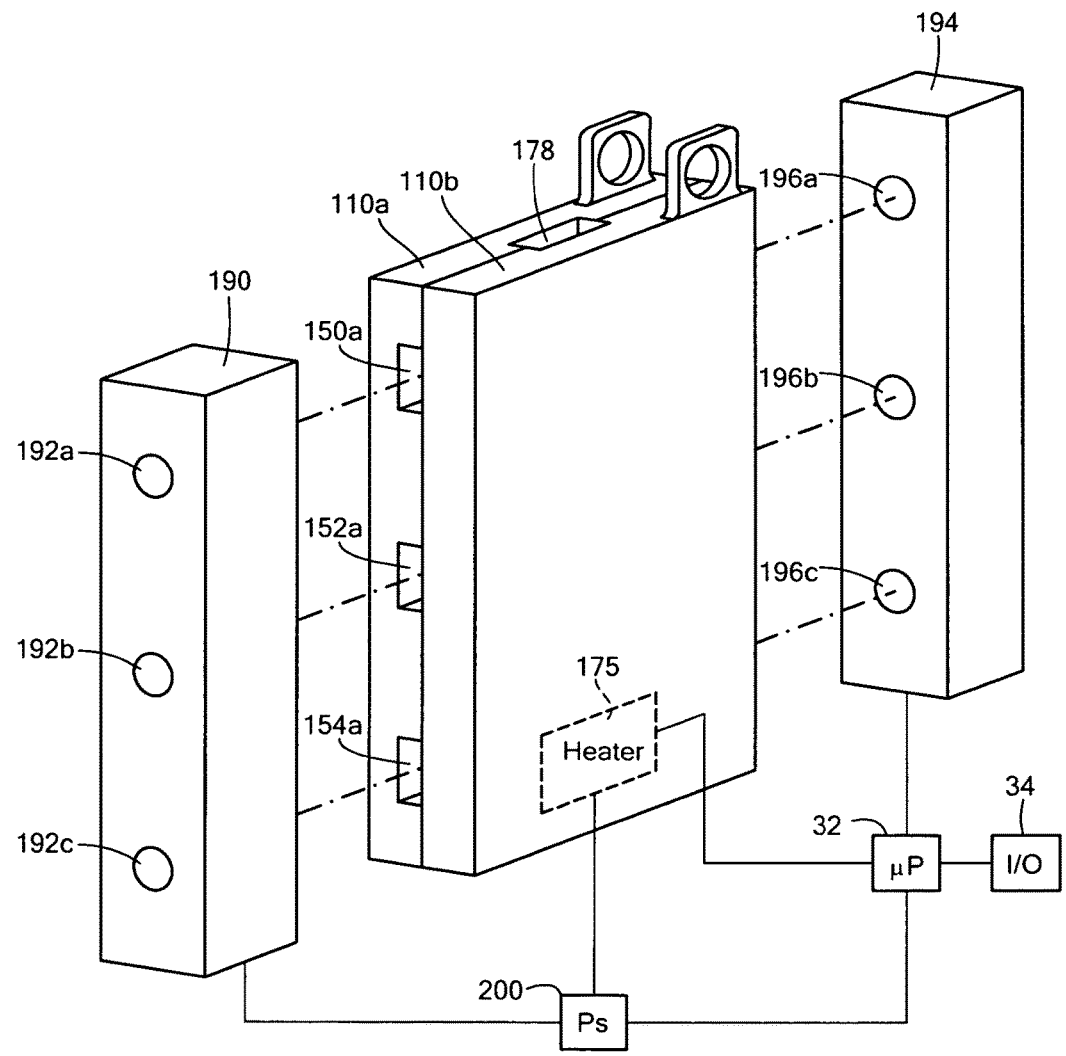
FIG. 6 is a schematic depiction of an example of a viscometer analysis subsystem of the system shown in FIG. 2.

FIG. 6 depicts plates 110a and 110b coupled together and vertically disposed within the analysis unit which typically includes sources of electromagnetic radiation as shown at 190 with LEDs 192a, 192b, and 192c on one side of releasably coupled together plates 110a and 110b and detector assembly 194 with corresponding detector elements 196a, 196b, and 196c on an opposite side of plates 110a, 110b.

This arrangement allows for a measurement of the time it takes fluid on the top surface of rail 112a to move along rail 112 in order to thus provide a calculation of the velocity of the fluid on rail 112.

Sources 192 direct light through the gap between the rail and the surface spaced from the rail. A sample of a fluid is deposited at port 178 (defined by sloping ramp 62a in plate 110a and sloping ramp 166 in plate 110b, FIG. 4). The sample may be oil from an engine crank case or the like. The sample begins to flow under the force of gravity along rail 112, FIG. 4 and is constrained to the top surface of rail 112 via the design of rail 112 itself and the gap between rail 112 and surface 122 of plate 110b. LEDs 192a, 192b, and 192c, FIG. 6 direct light in channels 150a, 152a, and 154a, respectively, as shown. For example, the light from LED 192a is directed in channel 150a, FIG. 4, through the gap between the top of rail 112 and surface 122 of plate 110b, and then to channel 150b to be detected by detector 196a, FIG. 6. Light from LED 192b, in turn, is directed into channel 152a, FIG. 4, through the gap between the top of rail 112 and surface 122 of plate 110b, and then through channel 152b to be detected by detector 196b, FIG. 6. Similarly, light from LED 192c is directed into channel 154a, through the gap between the top of rail 112 and surface 122 of plate 110b, and then through channel 154b to be detected by detector 196c. The distance between the channels 150a, 152a, and 154a and/or the LEDs, and the like are known and thus, by using detectors 196a, 196b, and 196c, the time it takes the sample fluid to traverse known locations on rail 112 can be determined since detectors 196a, 196b, and 196c will no longer output a signal (or will output a different signal) indicating that they are detecting light from LED sources 192a, 192b, and 192c, respectively, when the oil on rail 112, FIG. 4 blocks or diffuses the light transmitted by the LED sources. Other sources of electromagnetic radiation can also be used including lasers.

The processing subsystem microprocessor or controller 32, FIG. 6 operates heater 175 via power source 200 (a battery pack behind panel 126, FIG. 2), and also, based on commands from input/output section 34, energizes the LEDs of transmitter 190 and reads the output from detector array 194 in order to calculate the velocity of the fluid moving in the gap between rail 112 and surface 122 of plate 110b, FIG. 4. Microprocessor or controller 32 then preferably uses the velocity to determine the kinematic viscosity according to the equation:

$$\text{Kinematic viscosity} = \text{gap thickness} * K * \text{accelerated due to gravity} * \frac{1}{\text{velocity}} \quad (1)$$

The gap is known (e.g., 100 μm), as is the constant K $$\left(\text{e.g. } \frac{1}{6}\right),$$

and the acceleration due to gravity. Other means for determining the kinematic viscosity of the fluid as a function of the predefined gap between the rail and surface 122 of plate 110b and the time it takes the fluid to flow along the rail are also within the scope of the subject invention. Microprocessor 32 can be programmed as set forth above and may reside in a portable computer of the like. The plates are then separated, the rail wiped clean, and then the viscometer is ready again for use. Processor 32 provides the viscosity information as a report to monitor 34 and can then provide one or more recommendations based on the fluid's viscosity and other properties.

Figure 7:
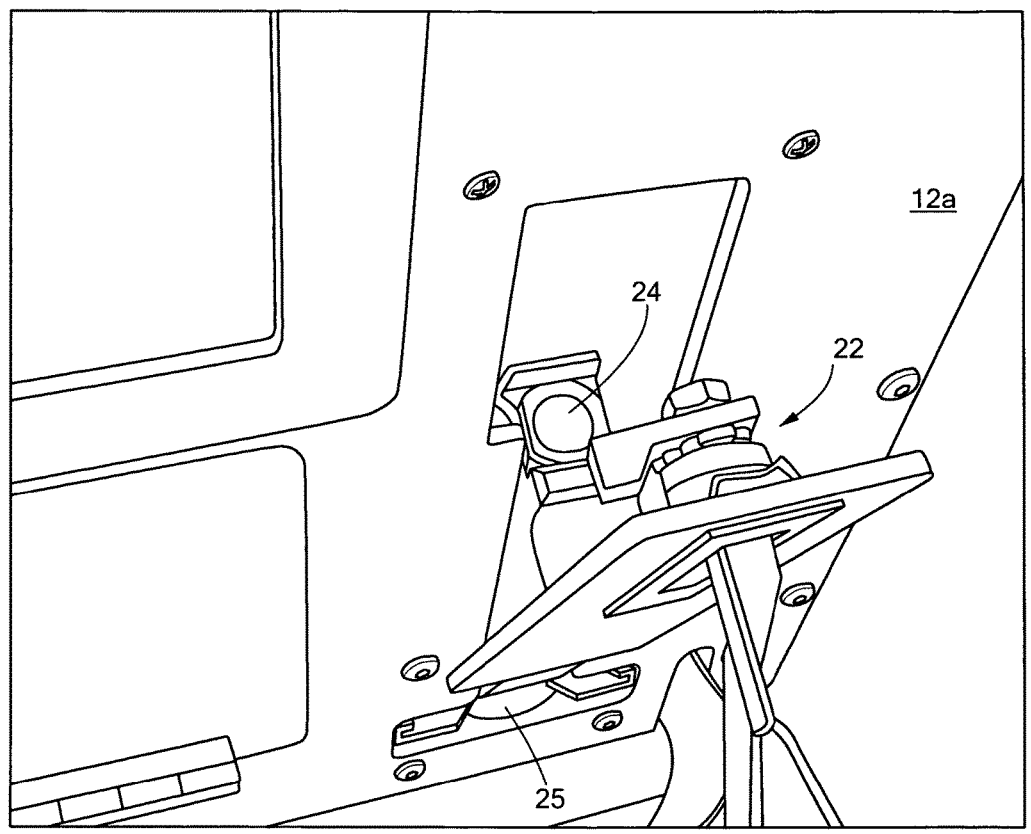
FIG. 7 is a schematic three-dimensional front view showing a portion of the syringe pump/particle counting subsystem of the system depicted in FIG. 2.
Figure 8:
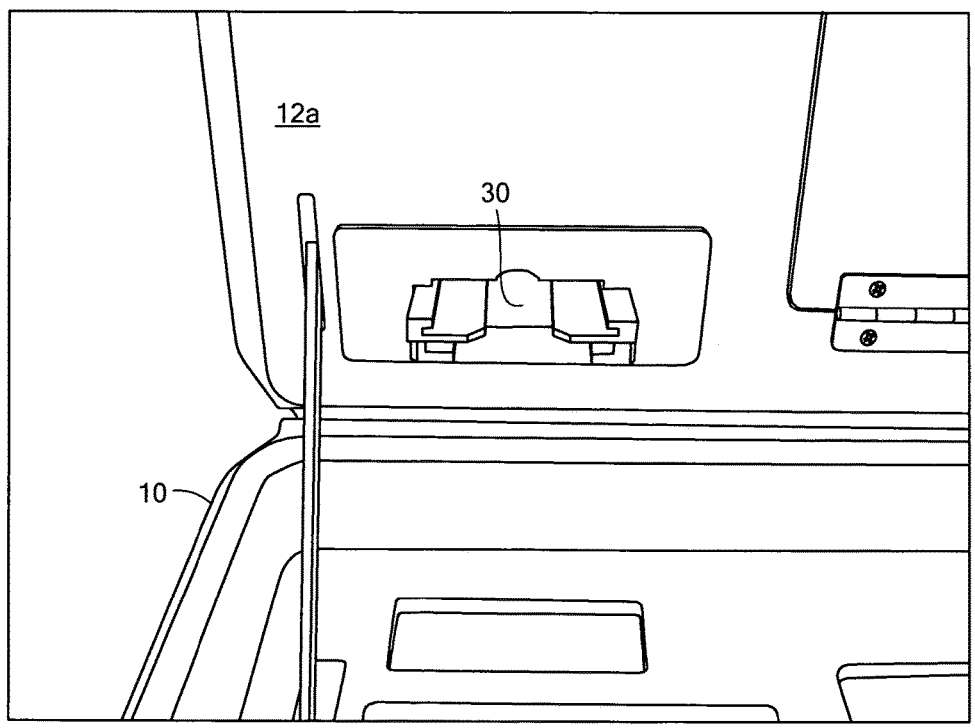
FIG. 8 is a schematic front view showing a cartridge port for the x-ray analysis subsystem of the system depicted in FIG. 2.

FIG. 7 shows fluid sample port 24 of syringe pump assembly 22 and cartridge port 25. FIG. 8 shows x-ray port 30.

Figure 9:
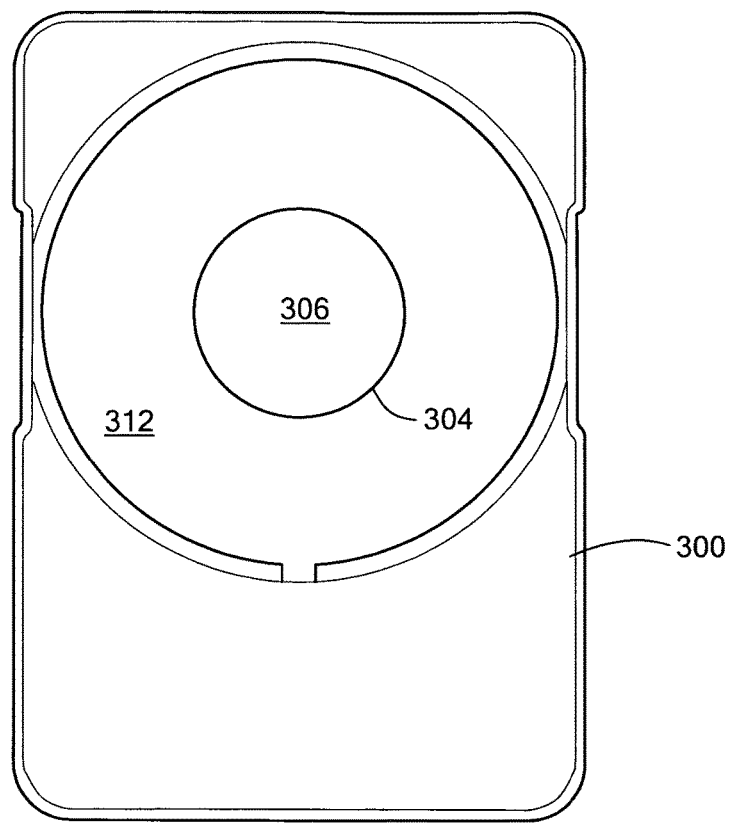
FIG. 9 is a schematic top view of an example of a particulate cartridge included with the analysis system of FIG. 2.
Figure 10:
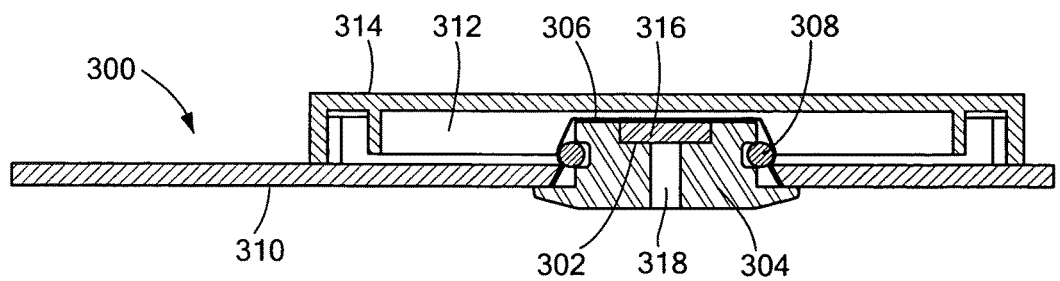
FIG. 10 is a schematic cross sectional side view of the particulate cartridge shown in FIG. 9.

FIGS. 9-10 show cartridge 300 preferably provided with the system for collecting and counting particulate matter in a sample via syringe pump subsystem in order to present the particulate matter to the x-ray analysis subsystem via port 30, FIG. 8. Cartridge 300 includes well 302 and filter holder 304 over which 0.005 in thick filter membrane 306 is disposed and held in place via band 308. Filter holder 304 is snap fit into plate 310 which features overflow well 312. Cartridge cover 314 may also be included in order to store a particular sample. In this example, felt material 316 fills well 302 and outlet port 318 is provided through filter holder 304 out of well 302 for excess sample fluid. Particulate cartridge 300 is placed in outlet port 25, FIG. 7 of syringe pump subsystem 22. A liquid sample is placed in port 24 and the syringe pump subsystem drives fluid through membrane 306, through wick 316, and into outlet 318 to be collected in a bladder associated with the syringe pump subsystem. Particulates present in the sample are counted using ISO-based techniques, and a calibrated amount now resides on filter membrane 306. For example, the syringe may have the capability of dispensing 3 ml of fluid. However, while the syringe is in the process of dispensing, if the particle counting aspect of the syringe pump detects a particle count above a pre-defined threshold, the pump may automatically stop at, say 0.5 ml of dispensed fluid, since dispensing any more fluid may cause too make particles to "cake" on the membrane, and obscure collected particles which reside closest to the membrane itself from x-ray analysis, which can lead to significant errors in the x-ray analysis. Particles deposited for x-ray analysis onto a membrane may give varying signals based on the amount deposited. The present invention mitigates this by controlling the number of particles that are deposited on the membrane. This particle counting thus serves the dual purpose of providing ISO-based particle counting to the user along with optimizing the profile of the x-ray membrane for analysis.

The technician then removes cartridge 300 from syringe pump subsystem port 25, FIG. 7 and places cartridge 300 in x-ray analysis subsystem port 30, FIG. 8. The x-ray analysis subsystem is then activated and the particles x-rayed, identified, and quantified.

Figure 11:
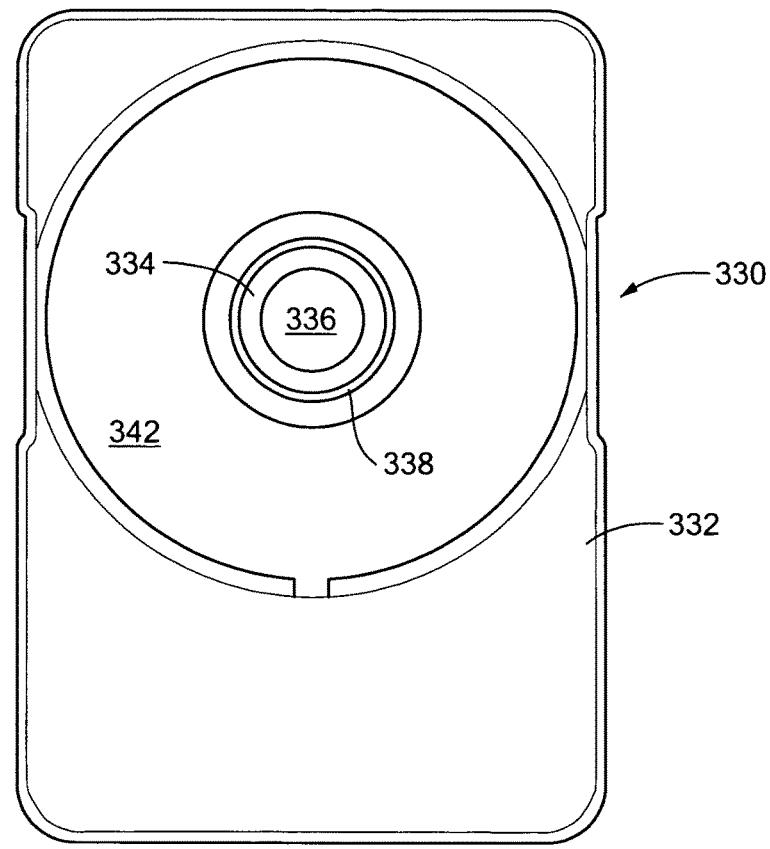
FIG. 11 is a schematic top view of a liquid sample cartridge included with the analysis subsystem of FIG. 2.
Figure 12:
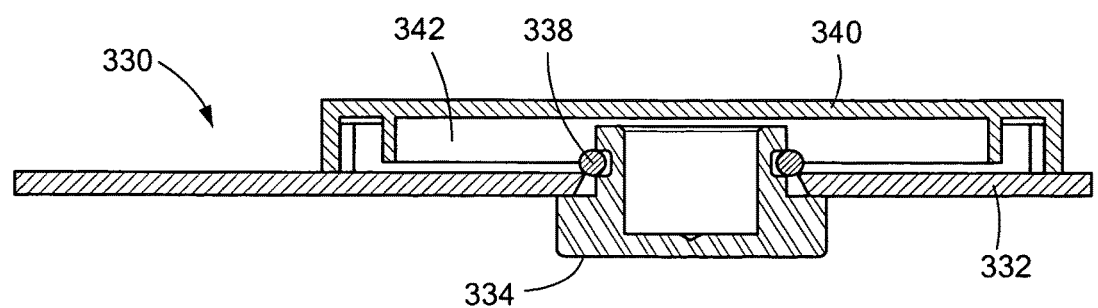
FIG. 12 is a schematic cross sectional side view of the liquid sample cartridge shown in FIG. 11.

FIGS. 11-12 depict another cartridge 330 provided with the system. Liquid cartridge 330 includes plate 332 and sample cup 334 with well 336. Sample cup 334 is retained in plate 332 via a spring, band or o-ring 338. Cover 340 may also be provided in order to store a particular sample. Plate 32 may also define overflow well 342.

A portion of the sample is delivered to well 36 of liquid sample cartridge 330 using a syringe and liquid sample cartridge 330 is then placed in port 30, FIG. 8 of the x-ray analysis subsystem which is then used to x-ray and provide data concerning dissolved material in the liquid sample (identification and quantification).

Figure 13:
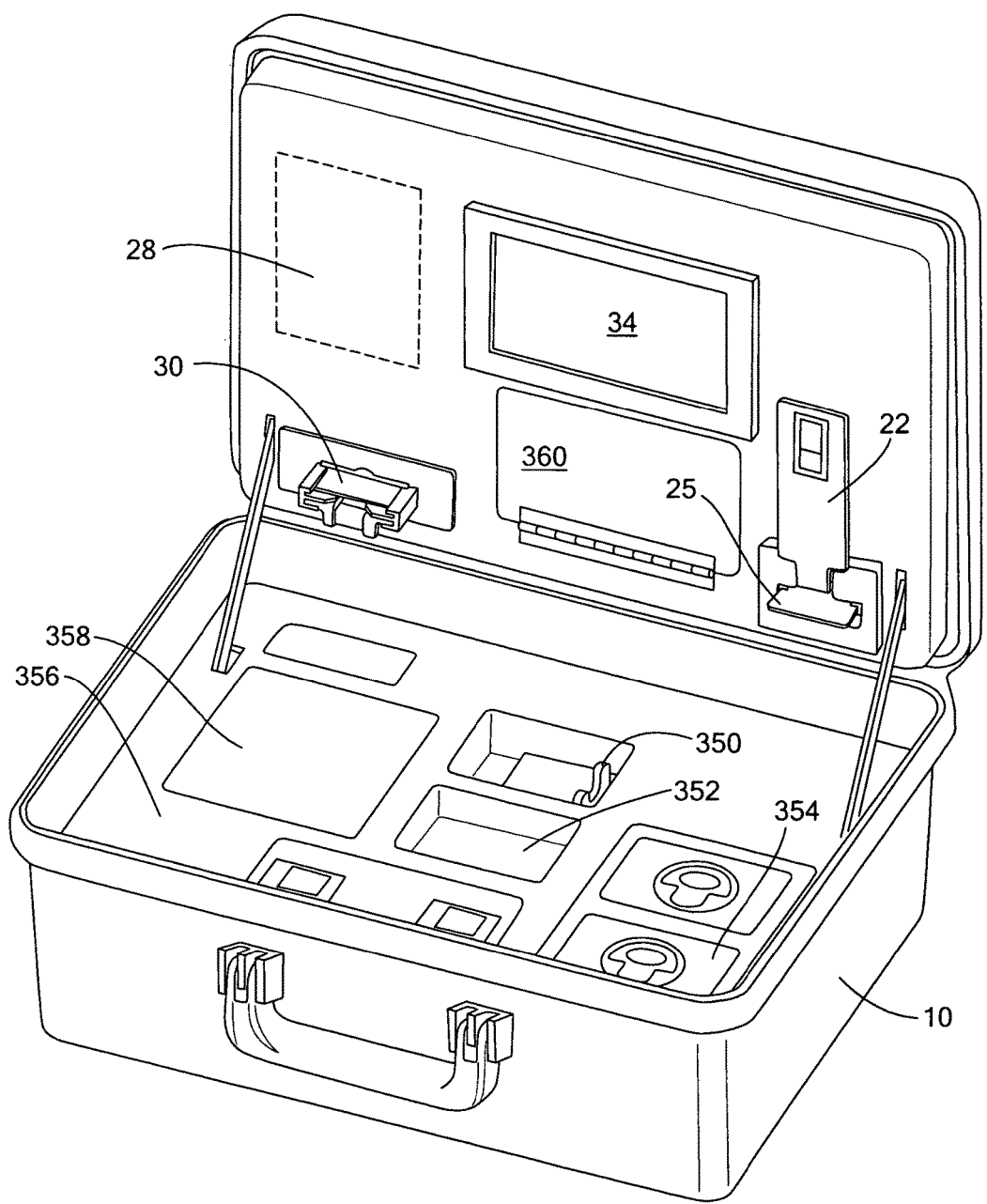
FIG. 13 is a schematic three dimensional front view showing one example of an integrated portable sample analysis system in accordance with the invention.

FIG. 13 depicts a prototype system within portable case 10. X-ray subsystem 28 is shown, typically an x-ray fluorescence type subsystem. Also shown is syringe pump subsystem 22 and 7 in LCD monitor 34. In the bottom portion of case 10 is a compartment or station 350 for infrared spectrometer subsystem 14, FIGS. 1-2. The viscometer subsystem is located in viscometer load station 352. The rechargeable battery pack is located behind panel 354 and provisions are made for waste storage as shown at 356. Samples, cartridges, and the like can be stowed in sample storage area 358. The electronics associated with the subsystem including the computer software, a database, and a controller or processing subsystem are located behind access panel 360.

Figure 14:
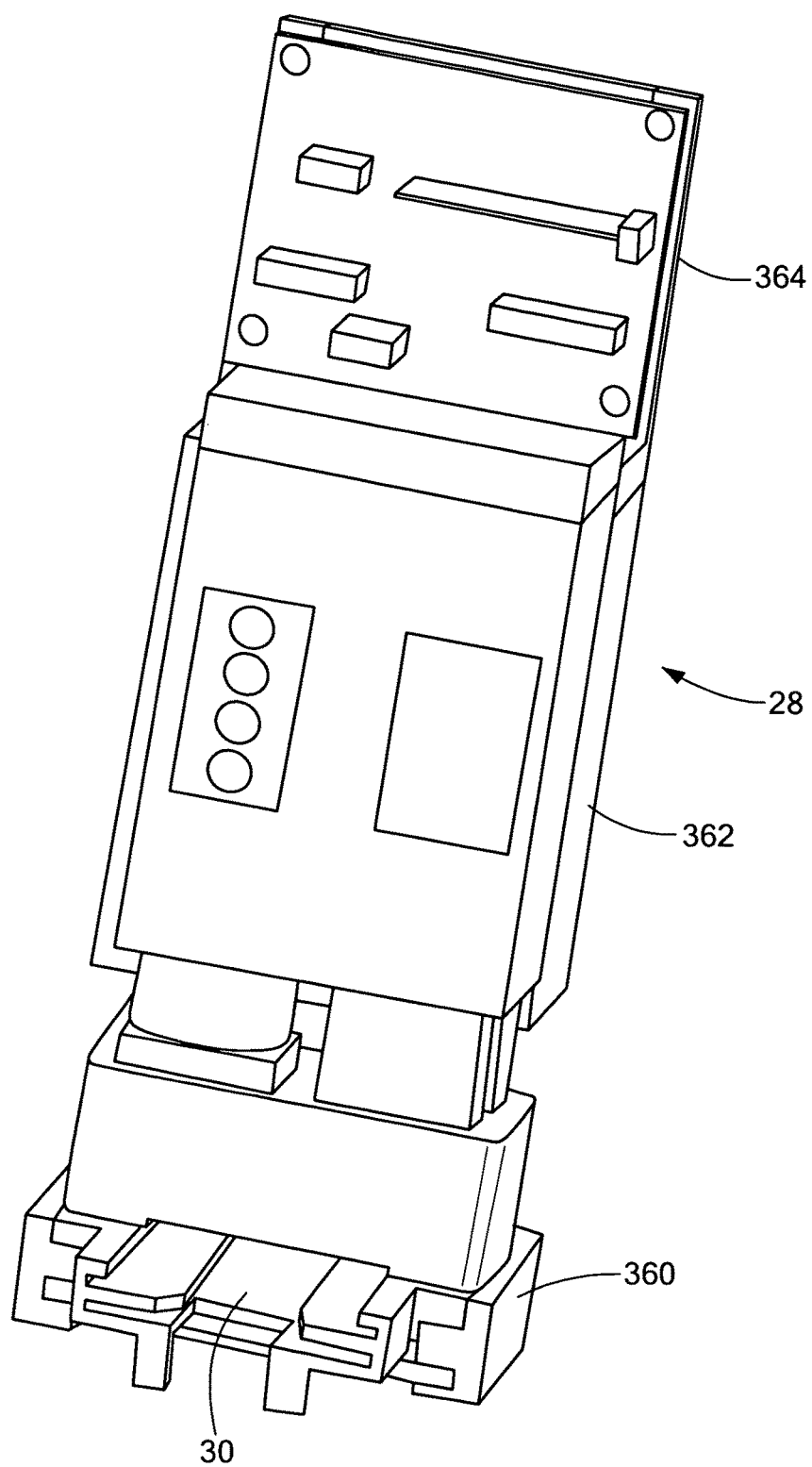
FIG. 14 is a schematic front view showing the primary components associated with the x-ray analysis subsystem of the system of the invention.
Figure 15:
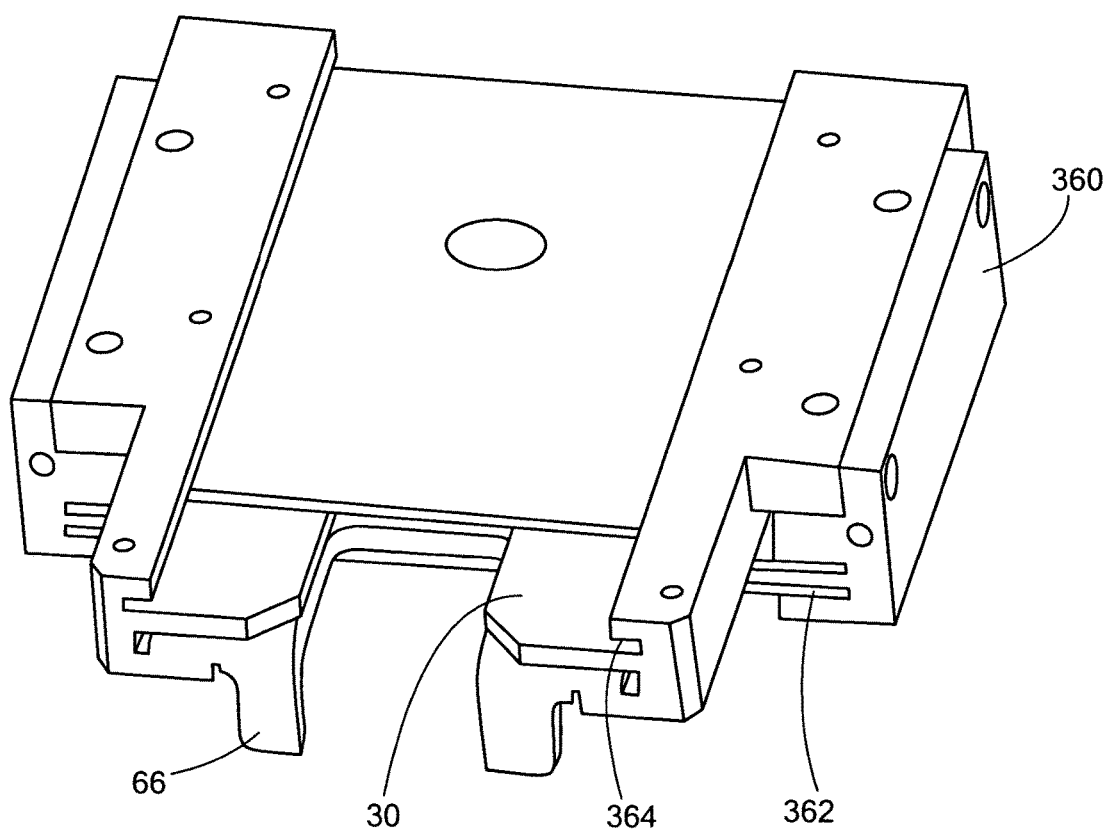
FIG. 15 is a schematic view of the particulate and liquid sample cartridge holder component of the x-ray analysis subsystem shown in FIG. 14.

FIG. 14 shows the configuration of x-ray analysis subsystem 28 and x-ray slide holder component 360. An x-ray source and detector are typically located within module 362 and the controlling electronics for the x-ray analysis subsystem is located as shown at 364. X-ray slide holder 360 is also shown in FIG. 15 and again, as discussed above, defines port 30 for the two cartridges discussed with reference to FIGS. 9-12. Typical components of this module include x-ray stop filter 362, slide-grooves for the sample cartridges 364, and removable drip tray 366.

Figure 16:
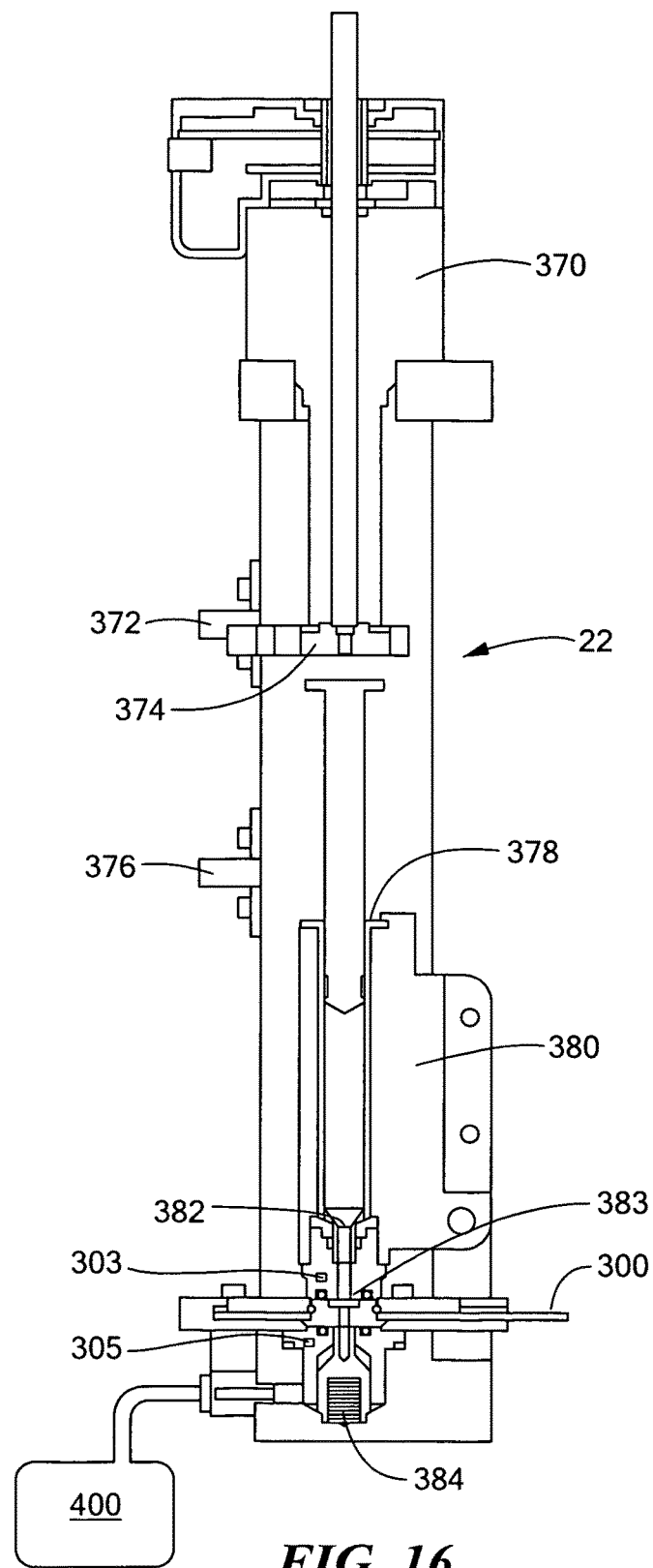
FIG. 16 is a schematic cross sectional front view showing several of the components associated with the syringe pump subsystem of the invention.

FIG. 16 depicts several of the primary components associated with a typical syringe pump assembly including linear actuator 370, rear position sensor 372, syringe pusher 374, front position sensor 376, syringe 378, syringe holder 380, syringe stop 382. Particulate cartridge 300 (see FIGS. 9-10) is shown in place below syringe 378. Below the cartridge is drain block 384 connected to bladder 400 for excess sample fluid exiting port 318, FIG. 10 of the particulate cartridge. Pressure transducers located at 383 provide the inputs needed for the particle counting. A feedback-based algorithm monitors these pressures and adjusts the motor speed as necessary to provide an accurate particle count for a wide range of viscosities.

A pressure differential between fluid above and below the cartridge membrane (306, FIG. 10) is a function of how many particles occupy the membrane or the density of the particles on the membrane. When the particles fill the pores of the membrane, a second layer of particles begins to build up on the membrane and x-raying the particles becomes more difficult. Conversely, too few particles results in a low x-ray signal and, again, difficulty in analyzing the particles.

By including a pressure sensor 303, FIG. 16 responsive to pressure $P_1$ of the fluid in the syringe above the filter membrane and another pressure sensor 305 below the filter membrane responsive to pressure $P_2$ of the fluid in the syringe below the membrane, the amount of particles which occupy the membrane (i.e., their density) can be determined. For example, a comparator function of the processing subsystem can calculate the absolute value of the difference between $P_1$ and $P_2$ and stop actuation of the syringe pump when the pressure difference is greater than a pre-established value (for example, 10 psi). The processing subsystem is also typically programmed to alert the user (using a screen prompt or indicator lamp, for example,) that the cartridge is now ready for insertion into the x-ray subsystem (28, FIGS. 1, 13, and 14) when the syringe pump is stopped after the pressure differential reaches the pre-established value.

In the laboratory, a determination of the solids in a sample would include acid digestion to transfer the solids in liquid form for an analysis by x-ray techniques and the like.

In the subject invention, solids (particles) are analyzed two ways: 1) the filtered particles (above a predetermined size) are x-rayed at a lower power using the filter membrane cartridge discussed above placed in the x-ray port (30, FIG. 1) and 2) the smaller dissolved particles which pass through the filter membrane (see bladder 400, FIG. 10) are placed in solution form in cartridge 330, FIGS. 11-12 (within well 336) and introduced into x-ray port 30, FIG. 1. These dissolved particles are x-rayed at a higher power.

The result is analysis and identification of particles below and above a certain size (e.g., below and above 10 microns). The processing subsystem is preferably programmed to automatically energize the x-ray source at a lower power (e.g., 0.5 Watts) when the particle cartridge of FIGS. 9-10 is introduced into port 30, FIG. 14 and to energize the x-ray source at a higher power (e.g., 4 Watts) when the solution cartridge of FIGS. 11-12 is introduced into port 30, FIG. 14.

Figure 17:
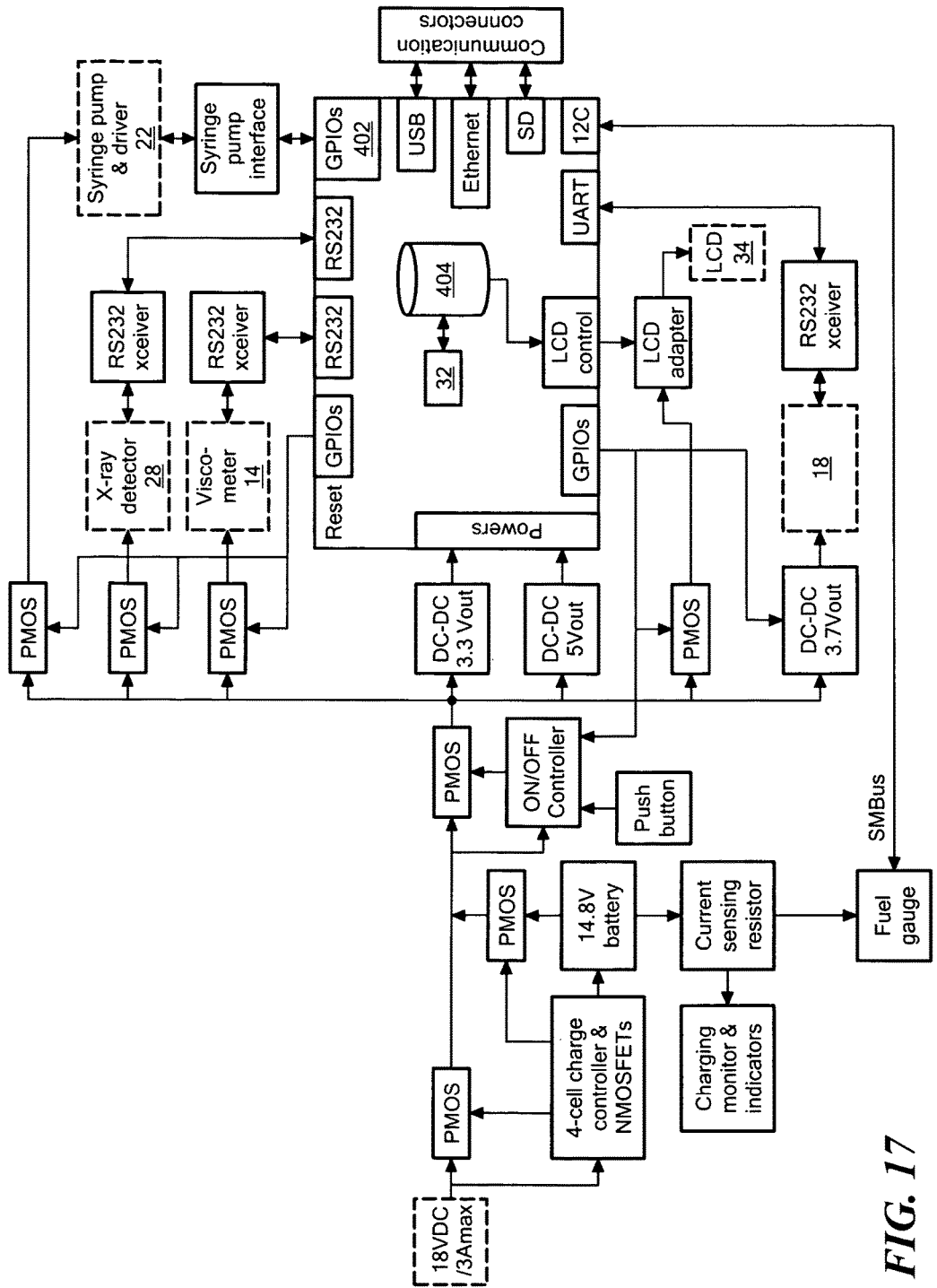
FIGS. 17-18 are block diagrams showing the architecture of the primary components associated with a sample analysis system in accordance with the invention.
Figure 18:
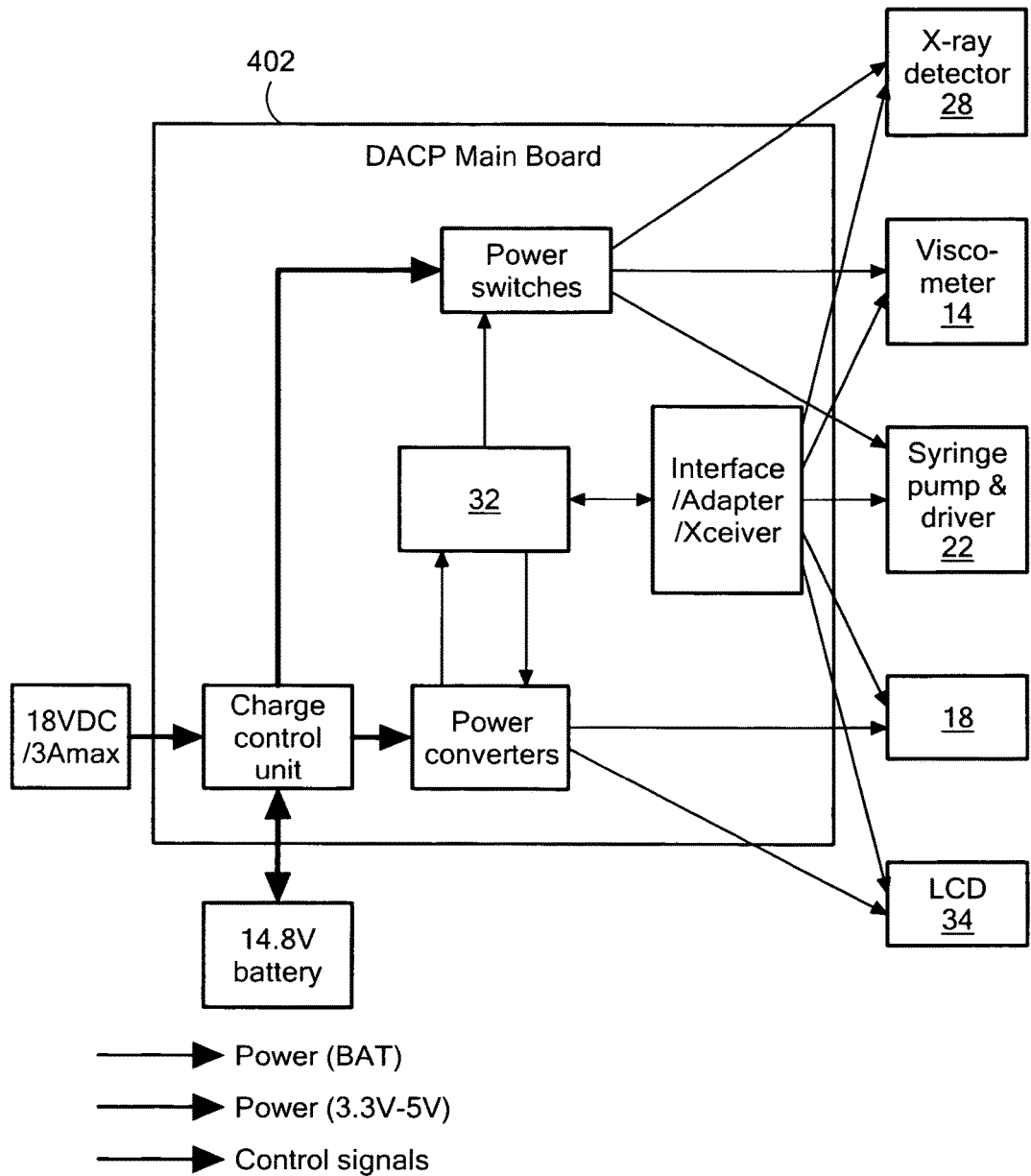

FIGS. 17-18 show some of the primary components associated with the system including processing subsystem board 402 itself including one or more processors 32 and memory devices for database 404. The connection between x-ray detector 28, the viscometer 14, the syringe pump and particle counting subsystem 22, the spectrometer 18, the LCD screen 34, and the like is also shown.

The system software operating on processor 32 is preferably an asset-based system. In other words, each measurement suite is tied to a particular asset (for example, the main diesel engine of a dump truck). Information about that asset is stored in a SQL database 404 stored in RAM, for example. Once a measurement suite takes place, the system software retrieves information associated with that asset and compares it to the measured values. In a typical configuration, this will include high-and-low limit values for each property measured. The software performs the comparison to the high-and-low limit values and the measured values and reaches a conclusion at three levels: One, at the specific property level (e.g., viscosity or Fe content), two, at the instrument level (IR, viscosity, x-ray, particle count), and three, at the overall recommendation level. The conclusion reached is configured to be at 3 levels: all OK, warning, and alarm. If any specific property associated with an instrument is in an alarm or warning state, the worst state of all properties will be reflected at the instrument level recommendation. Similarly, the worst state of any particular instrument will be reflected at the overall recommendation level.

The software is configured such that the overall recommendation is simply an "OK" check mark for good, a warning sign for warning and a red circle with a slash though it for an alarm state. This is shown in the sample report screens of FIGS. 19A and 19B. Specific properties are reported in green, red and yellow to reflect their particular status. In this way, the user can visually see which parameters are causing the fluid analysis to fail and take appropriate action. The user can scroll through the detailed temporal history of a particular asset by simply touching the LCD screen and moving through each sample over time. The histories are aligned in column format on-screen so that it is easy to compare nearby in time measurements of the same quantity as well as overall fluid status side-by-side. It is also possible to view measurements in time series without regard to asset. In addition, the reporting feature allows for x-y plotting of any particular property over time for that asset in order to gain knowledge of trends that might be occurring in the fluid which can reflect trends in the asset itself. All of this is available through the device touchscreen. At any point in time, the particular information cluster that has been generated on-screen may be sent to a printer for hard-copy documentation.

The software works to feed information into this reporting structure by initiating and collecting measurements from each individual system instrument. The individual instrument information is gathered by the software and archived automatically in the on-device SQL database. In general, the raw information from each instrument is turned into measurement information (e.g. amount of water or Si in ppm) by the system software. This is the information which populates the reporting section and is also archived in the same on-device SQL database. The system software allows for the creation of a measurement suite for a particular asset in order to streamline the measurement process. This information is stored in the database as unique asset information. For example, the user may not be interested in the viscosity of certain very low viscosity fluids (e.g., hydraulic fluids), so an asset which employs hydraulic fluids may be set up such that its measurement suite only includes IR and x-ray measurements. The menus and measurement navigation are changed automatically to reflect the measurement suite of the particular asset under test.

Figure 19B:
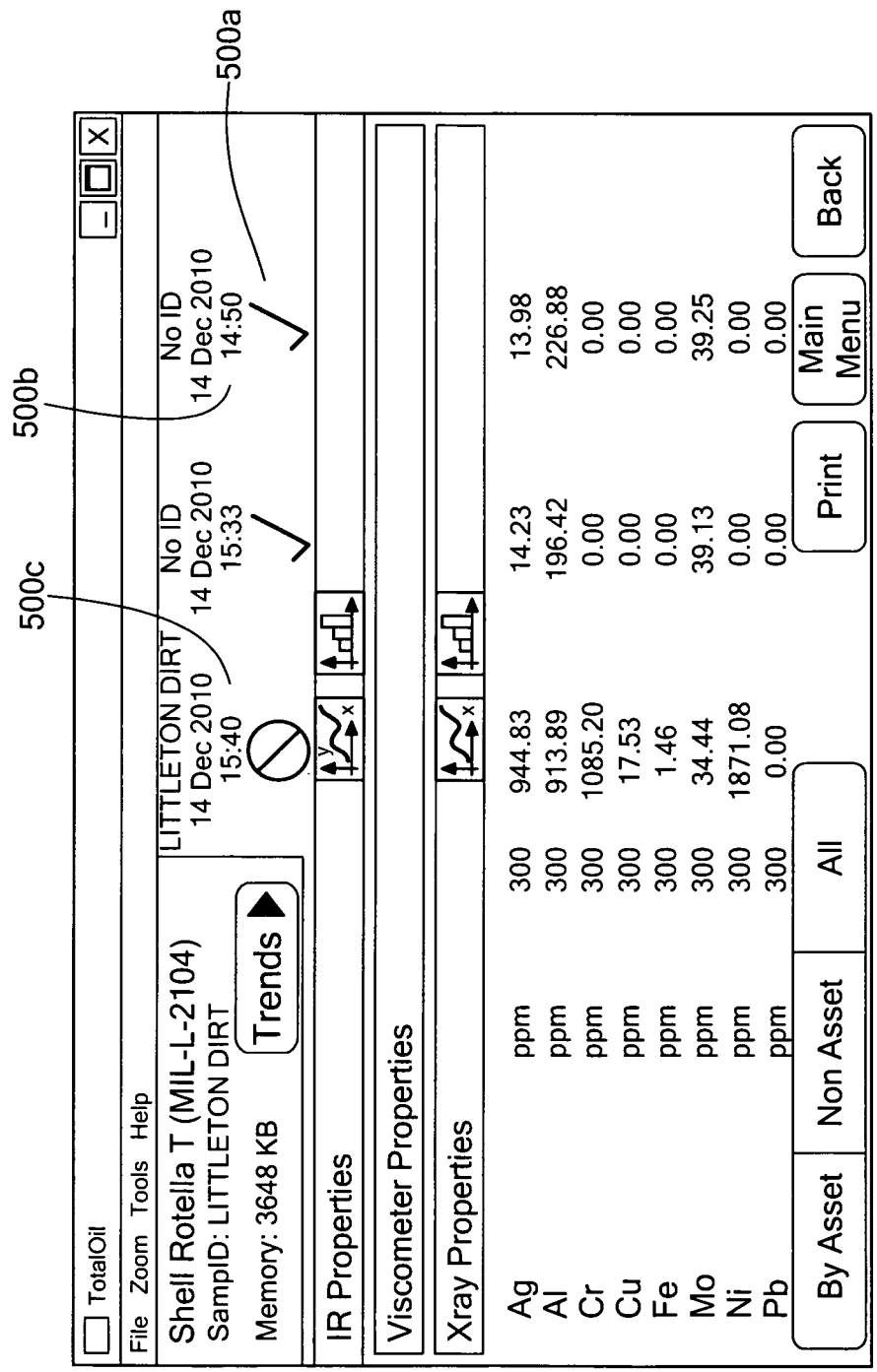

FIGS. 19A-19B depict examples of reports provided on LCD monitor 34, FIGS. 13 and 17. The infrared spectrometer subsystem provides signals enabling the computer software operating on the processing subsystem to generate data such as shown under the heading "IR Properties" in FIG. 19A. The viscometer subsystem provides an output enabling the computer software to provide viscosity data as shown under "viscometer properties" in FIG. 19A. The x-ray subsystem outputs data enabling the computer software to display the data shown under the heading "X-Ray Properties" in FIG. 19B. In this particular report, the total amount of iron, aluminum, silver, and the like is displayed which includes the amount of dissolved matter within the fluid sample as well as the amount of matter in a particulate state as present on the filter of particulate cartridge 300 discussed above with reference to FIGS. 9-10. The system enables the operator to generate a report, for example, on just the particulates present in the sample and/or the amount of dissolved material present in the sample as output by the x-ray analysis subsystem.

The processing subsystem is preferably configured (e.g., programmed) to highlight data and report data above a predetermined threshold and/or below a predetermined threshold. In the example shown in FIG. 19B, the amount of silver, aluminum, chromium, and nickel has exceeded their respective preset maximum amounts (in parts per million) and thus they are highlighted or shown, for example, in red letters as opposed to the white letters for the amount of copper, iron, and the like lead which are within their respective tolerances and hence depicted in white numbers. The processing system is also configured to analyze any of the highlighted or out of tolerance data to provide a "grade" for the sample based on the highlighted data. As shown for earlier samples at 500a and 500b, the overall report is a green check mark meaning all of the data was within specified limits. The report grade as shown for the sample at 500c, however, shows a warning or danger icon depicting a failing grade for the particular sample. For a given asset such as an engine, the oil can be sampled at different times and trends noted as shown in FIG. 19B where there has been a severe increase in the amount of chromium in the oil sample when compared to previous samples at earlier times.

The result is a portable and highly integrated sample analysis system and method wherein a sample is analyzed using several instruments and the analysis information is processed in order to note important information about the sample and/or the equipment from which the sample originated. The system of the subject invention can be operated by a less-skilled worker. The carrying case of the portable system is designed in such a way that four portions of the sample can be presented to different instruments and then the processing subsystem provides a report concerning, for example, the sample and its viscosity, its physical properties, particulates and dissolved material. One or more recommendations can even be made based on the sample's viscosity, physical properties, particulates and the composition of any dissolved materials in the sample. Further, the operator does not need to use chemicals, solvents or diluents of any kind in order to operate the system. He or she simply wipes the viscometer and IR subsystems clean with a shop rag, and the entire system is ready for its next measurement. This makes the device particularly useful for operation in remote locations or where chemicals are not readily available, and significantly enhances its portability.

In use, a technician takes a sample from an apparatus on site (e.g., oil from an engine crankcase) and uses a syringe to place a first-portion of a sample in viscometer 18, FIG. 2. The viscometer subsystem analyzes the first portion of the sample and provides a signal corresponding to the viscosity of the sample to the processing subsystem. The technician next places a second portion of the sample in spectrometer subsystem 14 and it analyzes the second portion of the sample and provides one or more signals corresponding to physical properties of the sample to the processing subsystem. A third portion of the sample is delivered to syringe pump subsystem 22 where particles are counted and filtered out of the third portion of the sample. The particles are analyzed by the x-ray analysis subsystem which provides one or more signals corresponding to the composition of the particles to the processing subsystem. A fourth (e.g., liquid) portion of the sample is also delivered to the x-ray analysis subsystem which analyzes the fourth portion of the sample and provides one or more signals corresponding to dissolved material in the sample. The signals corresponding to the viscosity of the sample, the physical properties of the sample, the composition of the particles, and the dissolved materials in the sample are processed and a report is automatically generated at the site concerning the sample and its viscosity, physical properties, particulates and dissolved materials. Also, the processing subsystem automatically highlights information at the site based on the viscosity, physical properties, particulates, and dissolved material of the sample.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. An integrated, portable analysis case comprising in the portable analysis case:
   a flip top cell viscometer including:
      a first plate including a raised rail in communication with a first well, the raised rail for receiving a first portion of a fluid sample manually deposited into the first well, and
      a second plate including a surface spaced from the rail by a predetermined gap which, in conjunction with the raised rail, constrains the fluid to the raised rail by surface tension when the rail is inclined such that the fluid flows along the rail by gravity to determine the viscosity of the fluid sample;
   a flip top cell spectrometer subsystem including:
      a first plate with a first window;
      a second plate with a second window aligned with the first window, and
      a predefined spacing between the first and second windows configured as a second well for receiving a second portion of the fluid sample manually deposited to the second well to determine properties of the fluid sample;
   a particle counter including:
      a particle cartridge including a filter, and
      a syringe pump configured to pump a third portion of the fluid sample manually loaded therein through the cartridge filter to count particles in the fluid sample the syringe pump including a syringe pusher, a syringe holder, a pressure sensor upstream of the cartridge filter, and a pressure sensor downstream of the cartridge filter;
   a x-ray analysis subsystem configured to x-ray a portion of the fluid sample present on a cartridge manually loaded into the x-ray analysis subsystem to determine the concentration of metals in the fluid sample;
   a processing subsystem responsive to the viscometer, the spectrometer subsystem, the particle counter, and the x-ray analysis subsystem and configured to provide a report concerning the viscosity of the fluid sample, properties of the fluid sample, a particle count for the fluid sample, and the concentration of metals in the fluid sample; and
   a monitor for displaying said report.

2. The case of claim 1 in which the particle cartridge includes a third well covered with said filter.

3. The case of claim 2 in which the third well further includes an outlet port.

4. The case of claim 2 in which said third well includes a wick.

5. The case of claim 3 in which the particle counter further includes a bladder for receiving the third portion of the sample which flows out of the outlet port of the third well.

6. The case of claim 1 further including a liquid sample cartridge including a fourth well for a fourth portion of the sample and configured to be inserted into the x-ray analysis subsystem.

7. The case of claim 1 further including a panel in the case housing the viscometer and the spectrometer subsystem.

8. The case of claim 7 further including another panel in the case housing the particle counter and x-ray analysis subsystem.

9. The case of claim 1 further including a battery pack for the viscometer, the spectrometer subsystem, the particle counter, the x-ray analysis subsystem, and the processing subsystem.

10. The case of claim 1 in which the processing subsystem is configured to highlight data in the report above a predetermined threshold and/or below a predetermined threshold.

11. The case of claim 10 in which the processing subsystem is further configured to analyze any highlighted data and to provide a grade for the sample based on said highlighted data.

12. The case of claim 1 in which the processing subsystem is responsive to the pressure sensors and configured to stop actuation of the syringe pump when a pressure differential upstream and downstream of the filter reaches a predetermined value.

13. The case of claim 1 in which the processing subsystem is further configured to automatically energize the x-ray analysis subsystem at a first, lower power when x-raying particles and to energize the x-ray analysis subsystem at a second, higher power when x-raying dissolved material.

14. A sample analysis method comprising:
   manually taking a fluid sample from an apparatus at a site;
   manually placing a first-portion of a fluid sample in a flip top cell viscometer having a first plate with a raised rail spaced from a surface of a second plate by a predetermined gap which, in conjunction with the raised rail constrains the fluid to the raised rail by surface tension when the rail is inclined;
   automatically analyzing the first portion of the fluid sample in the viscometer and providing a signal corresponding to the viscosity of the sample based on the velocity of the fluid moving along the raised rail due to gravity;
   manually placing a second portion of the fluid sample in a flip top cell spectrometer;

automatically analyzing the second portion of the fluid sample in the spectrometer and providing one or more signals corresponding to physical properties of the sample;
manually placing a third portion of the sample in a syringe;
manually inserting a cartridge with a filter into a particle counter;
manually inserting the syringe into a syringe pump,
driving the syringe pump to deposit particles in the third portion of the fluid sample on the cartridge filter;
determining a particle count;
providing a signal corresponding to the particle count;
manually placing a portion of the fluid sample on a cartridge;
manually placing the cartridge in an x-ray analysis subsystem, x-raying the fluid and providing one or more signals corresponding to metals in the fluid sample; and
automatically processing the signals corresponding to the viscosity of the sample, the properties of the sample, the particle count, and the metals in the fluid sample; and
automatically generating a report at the site concerning the sample and its viscosity, properties, particle count, and metals.

15. The method of claim 14 further including highlighting data in the report above a predetermined threshold and/or below a predetermined threshold.

16. The method of claim 15 further including grading the sample based on said highlighted data.

17. The method of claim 15 further including the step of measuring the pressure upstream of the filter and downstream of the filter to determine when the particles reach a predetermined density on the cartridge filter.

18. The method of claim 17 further including the step of stopping the filtering of the third portion of the sample when a pressure differential upstream and downstream of the filter reaches a predetermined value that ensures optimized x-ray analysis.

19. The method of claim 14 in which x-raying the fluid includes automatically energizing the x-ray analysis subsystem at a first, lower power when x-raying particles and automatically energizing the x-ray analysis subsystem at a second, higher power when analyzing dissolved material.

20. An integrated, portable analysis case comprising in the portable analysis case:
a flip top cell viscometer including:
a first plate including a raised rail in communication with a first well the raised rail for receiving a first portion of a fluid sample manually deposited into the first well, and
a second plate including a surface spaced from the rail by a predetermined gap which, in conjunction with the raised rail, constrains the fluid to the raised rail by surface tension when the rail is inclined such that the fluid flows along the rail by gravity to determine the viscosity of the fluid sample;
a flip top cell spectrometer subsystem including:
a first plate with a first window;
a second plate with a second window aligned with the first window, and
a predefined spacing between the first and second windows configured as a second well for receiving a second portion of the fluid sample manually deposited into a second well to determine properties of the fluid sample; and
a processing subsystem responsive to the viscometer and the spectrometer subsystem and configured to provide a report concerning the viscosity of the fluid sample, and properties of the fluid sample.

21. The integrated, portable analysis case of claim 20 further comprising:
a particle counter including:
a particle cartridge including a filter, and
a syringe pump configured to pump a portion of the fluid sample loaded into a syringe through the cartridge filter to count particles in the fluid sample;
a x-ray analysis subsystem configured to x-ray a portion of the fluid sample present on a cartridge loaded into the x-ray analysis subsystem to determine the concentration of metals in the fluid sample; and
the processing subsystem responsive to the particle counter and the x-ray analysis subsystem and configured to provide a report concerning a particle count for the fluid sample and the concentration of metals in the fluid sample.

22. An integrated, portable analysis case comprising in the portable analysis case:
a flip top cell viscometer including:
a first plate including a raised rail in communication with a well, the raised rail for receiving a first portion of a fluid sample, and
a second plate hinged to the first plate and including a surface spaced from the rail by a predetermined gap which, in conjunction with the raised rail, constrains the fluid to the raised rail by surface tension when the rail is inclined such that the fluid flows along the rail by gravity to determine the viscosity of the fluid sample using sensors to determine the time it takes for the fluid to move along the rail;
a flip top cell spectrometer subsystem including:
a first plate with a first window;
a second plate hinged to the first plate and with a second window aligned with the first window, and
a predefined spacing between the first and second windows configured as a well for receiving a second portion of the fluid sample to determine properties of the fluid sample by spectroscopy after passing electromagnetic radiation passing through the first and second windows;
a particle counter including:
a particle cartridge including a filter, and
a syringe pump configured to pump a third portion of the fluid sample loaded therein through the cartridge filter to count particles in the fluid sample;
a x-ray analysis subsystem configured to x-ray a portion of the fluid sample present on a cartridge loaded into the x-ray analysis subsystem to determine the concentration of metals in the fluid sample; and
a processing subsystem responsive to the viscometer, the spectrometer subsystem, the particle counter, and the x-ray analysis subsystem and configured to provide a report concerning the viscosity of the fluid sample, properties of the fluid sample, a particle count for the fluid sample, and the concentration of metals in the fluid sample.

23. A sample analysis method comprising:
manually taking a fluid sample from an apparatus at a site;
manually placing a first portion of a fluid sample in a flip top cell viscometer having a first plate with a raised rail spaced from a surface of a second plate hinged to the first plate by a predetermined gap which, in conjunction with the raised rail, constrains the fluid to the raised rail by surface tension when the rail is inclined;

automatically analyzing the first portion of the fluid sample in the viscometer and providing a signal corresponding to the viscosity of the sample based on the velocity of the fluid moving along the raised rail due to gravity;

manually placing a second portion of the fluid sample in a flip top cell spectrometer having a first and second hinged plates each with a window;

automatically analyzing the second portion of the fluid sample in the spectrometer by spectroscopy after passing electromagnetic radiation through said windows and providing one or more signals corresponding to physical properties of the sample;

manually placing a third portion of the sample in a syringe;

manually inserting a cartridge with a filter into a particle counter;

manually inserting the syringe into a syringe pump, driving the syringe pump to deposit particles in the third portion of the fluid sample on the cartridge filter;

determining a particle count;

providing a signal corresponding to the particle count;

manually placing a portion of the fluid sample on a cartridge;

manually placing the cartridge in an x-ray analysis subsystem, x-raying the fluid and providing one or more signals corresponding to metals in the fluid sample; and automatically processing the signals corresponding to the viscosity of the sample, the properties of the sample, the particle count, and the metals in the fluid sample;

automatically generating a report at the site concerning the sample and its viscosity, properties, particle count, and metals; and wiping the raised rail of the flip top cell viscometer and the windows of the flip top cell spectrometer.

24. An integrated, portable analysis case comprising in the portable analysis case:

a flip top cell viscometer including:

a first plate including a raised rail in communication with a well, the raised rail for receiving a first portion of a fluid sample, and a second plate hinged to the first plate and including a surface spaced from the rail by a predetermined gap which, in conjunction with the raised rail, constrains the fluid to the raised rail by surface tension when the rail is inclined such that the fluid flows along the rail by gravity to determine the viscosity of the fluid sample using sensors to determine the time it takes the fluid to move along the rail;

a flip top cell spectrometer subsystem including:

a first plate with a first window;

a second plate hinged to the first plate and with a second window aligned with the first window; and a predefined spacing between the first and second windows configured as a well for receiving a second portion of the fluid sample to determine properties of the fluid sample by spectroscopy using electromagnetic radiation passing through the first and second windows;; and a processing subsystem responsive to the flip top cell viscometer and the flip top cell spectrometer subsystem and configured to provide a report concerning the viscosity of the fluid sample, and properties of the fluid sample.

25. The integrated, portable analysis case of claim 24 further comprising:

a particle counter including:

a particle cartridge including a filter, and a syringe pump configured to pump a portion of the fluid sample loaded therein through the cartridge filter to count particles in the fluid sample;

a x-ray analysis subsystem configured to x-ray a portion of the fluid sample present on a cartridge loaded into the x-ray analysis subsystem to determine the concentration of metals in the fluid sample; and the processing subsystem responsive to the particle counter and the x-ray analysis subsystem and configured to provide a report concerning a particle count for the fluid sample and the concentration of metals in the fluid sample.

* * * * *